US00PP24939P3

(12) United States Plant Patent
Quesada

(10) Patent No.: US PP24,939 P3
(45) Date of Patent: Sep. 30, 2014

(54) *SANSEVIERIA* PLANT NAMED 'WINTERGREEN'

(50) Latin Name: *Sansevieria trifasciata*
Varietal Denomination: Wintergreen

(71) Applicant: Florica Farms, Inc., Eustis, FL (US)

(72) Inventor: Julio Antonio Araya Quesada, Alajuela (CR)

(73) Assignee: Florica Farms, Inc., Eustis, FL (US)

( * ) Notice: Subject to any disclaimer, the term of this patent is extended or adjusted under 35 U.S.C. 154(b) by 84 days.

(21) Appl. No.: 13/694,409

(22) Filed: Nov. 30, 2012

(65) Prior Publication Data

US 2014/0157471 P1 Jun. 5, 2014

(51) Int. Cl.
*A01H 5/00* (2006.01)

(52) U.S. Cl.
USPC ..... Plt./382

(58) Field of Classification Search
CPC ..... A01H 1/00; A01H 1/04; A01H 1/06; A01H 4/00; A01H 4/05; A01H 4/008; A01H 5/08; A01H 5/00
USPC ..... Plt./382
See application file for complete search history.

*Primary Examiner* — Annette Para
(74) *Attorney, Agent, or Firm* — Foley & Lardner LLP

(57) ABSTRACT

The new variety 'Wintergreen' is part of the "long leaves *Sansevieria*" varieties. It can reach 80 cm in length, with an average of approximately 5-7 leaves per plant. The plant is cylindrically shaped, the arrangement of the leaves is in the form of a rosette. Shows colors very different from its parent variety ('Bantels Sensation', unpatented) Unlike its parent variety it shows variegated bands on the leaves, and the margins are dark green, as its parental variety, but 'Wintergreen' presents more leaves per rosette.

4 Drawing Sheets

Latin name of the genus and species of the claimed plant: *Sansevieria trifasciata.*

Variety denomination: Wintergreen.

BACKGROUND OF THE INVENTION

The present invention relates to a new and distinct cultivar of *Sansevieria* plant, botanically known as *Sansevieria trifasciata*, of the family Ruscaceae, hereinafter referred to by the cultivar name 'Wintergreen'.

*Sansevieria* is a monocotyledonous and succulent, flowering plant which can be produced in either hard-leafed or soft-leafed varieties for interior use as a house plant or outdoors ornamental plant.

The new *Sansevieria* 'Wintergreen' originated from a naturally-occurring mutation of the *Sansevieria* 'Bantels Sensation' (unpatented). The new *Sansevieria* 'Wintergreen' was discovered and selected by the inventor, Julio Araya Quesada, as a single sprouting rare mutated plant in a 'Bantels Sensation' plantation, a controlled environment, in 2007 in Bajo Los Rodriguez, San Ramón, Alajuela province, Costa Rica.

Asexual reproduction of the new *Sansevieria* cultivar by vegetative cuttings was first performed in July 2007 in Bajo Los Rodriguez, San Ramón, Alajuela, and demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Wintergreen', which in combination distinguish this *Sansevieria* as a new and distinct cultivar:

1. Moderate green colored foliage and light yellowish green bands in the leaf blade.
2. wide and lanceolate leaves, 60-90 cm long and supported in a rosette.
3. 60-90 cm plant height.
4. Plant habit: Erect.
5. Needs little water and is very drought tolerant.

The new variety 'Wintergreen' is considered a variety of *Sansevieria* in the group denominated as "long leaves *Sansevieria* varieties". The new variety presents an average of 5-7 leaves per plant when it reaches its maturity (between 8-10 months). The new variety has an erect growth habit and the entire plant can reach a height range between 60-90 cm. The leaves are narrow (3-5 cm average measured at the widest part of the mature leaf) and lanceolate, with a soft waxy texture. The blades are thin and slightly wavy. The plant has a cylindrical shape.

The new variety is moderately drought tolerant, adapts to conditions of light and shade (interior and exterior), and shows high resistance level to antrachnose (*Colletotrichum sansvierae*) disease.

The leaf blade is moderate green colored (RHS 135B), and presents also non-uniform horizontal variegated bands in both sides of the leaves, light yellowish green (RHS 138D) colored.

The variety 'Bantels Sensation' gave rise to the variety 'Wintergreen'. The 'Bantels Sensation' variety is also considered part of the "long leaves varieties" group. The claimed variety shows more vigor than 'Bantels Sensation', has a higher number of leaves per plant (5-7), with an average width of 3-5 cm (measured in the middle of the mature leaf.) The growth habit is erect and presents narrow leaves supported in a rosette. The entire plant can reach a size between 60-90 cm. The plant has, as for 'Bantels Sensation', a cylindrical shape.

Plants of the new *Sansevieria* 'Wintergreen' differ from plants of the parental cultivar, 'Bantels Sensation' (unpatented) in the characteristics described in Table 1.

TABLE 1

Comparison between 'Bantels Sensation' and 'Wintergreen'

| Characteristic | New Cultivar 'Wintergreen' | Parent 'Bantels Sensation' (unpatented) |
|---|---|---|
| Plant Vigor | more vigorous (more leaves) | less vigorous (less leaves) |
| Color | variegated leaves (light yellowish green cross-banding and green margins) | Very pale green leaves with deep green margins and longitudinal white streaks alternating with pale green lines. |
| Shape | narrow and lanceolated leaves on a rosette | narrow and lanceolated leaves on a rosette |
| Texture of leaves | smooth-textured leaves | smooth-textured leaves |

Of the many commercial cultivars known to the present inventor, the most similar in comparison to the new *Sansevieria* 'Wintergreen' is the parental cultivar, *Sansevieria* 'Bantels Sensation'.

BRIEF DESCRIPTION OF THE PHOTOGRAPHS

The accompanying photographs illustrate the overall appearance of the new *Sansevieria* cultivar 'Wintergreen' showing the colors as true as is reasonably possible with colored reproductions of this type. Colors in the photographs may differ slightly from the color value cited in the detailed botanical description which accurately describe the color of 'Wintergreen'.

DETAILED BOTANICAL DESCRIPTION

Figure 1:
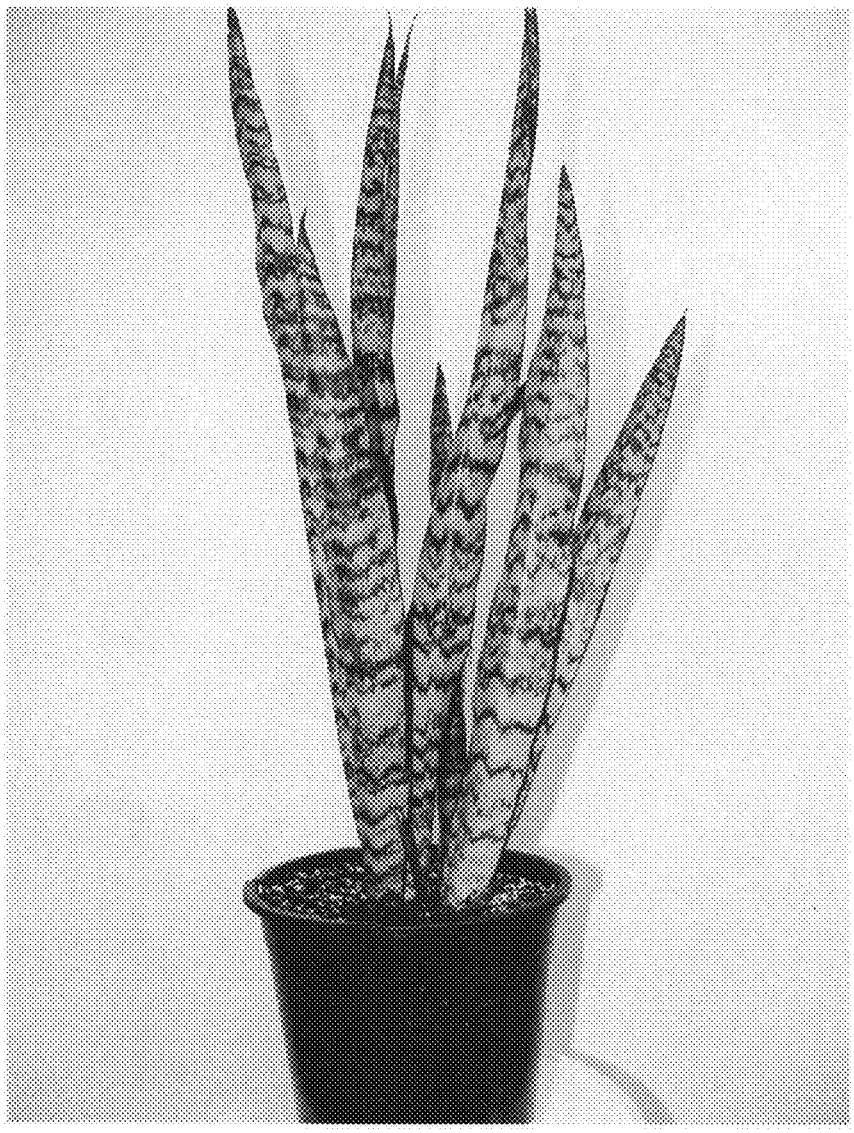
FIG. 1 shows a side view of an eight-month old plant of *Sansevieria* 'Wintergreen' in a 21 cm diameter pot.
Figure 2:
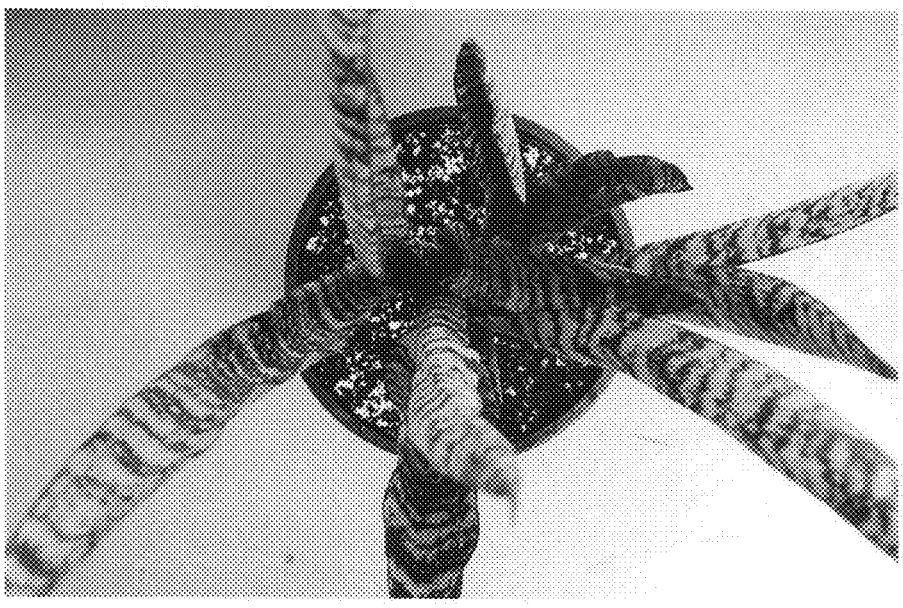
FIG. 2 shows a top view of an eight-month old plant of *Sansevieria* 'Wintergreen' in a 21 cm diameter pot.
Figure 3:
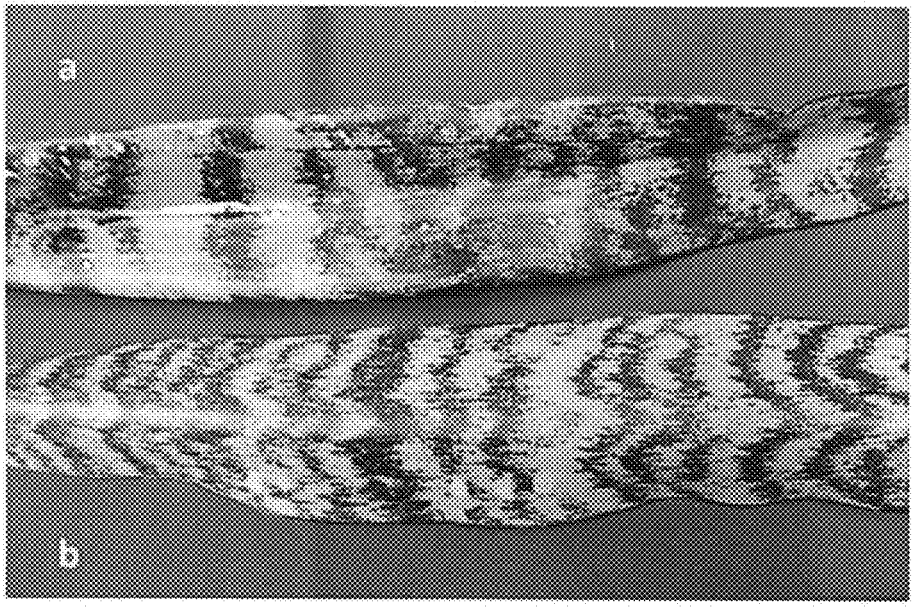
FIG. 3 shows a close-up view of the typical leaves of 'Wintergreen' from an eight-month old plant (upper side—A, under side—B).
Figure 4:
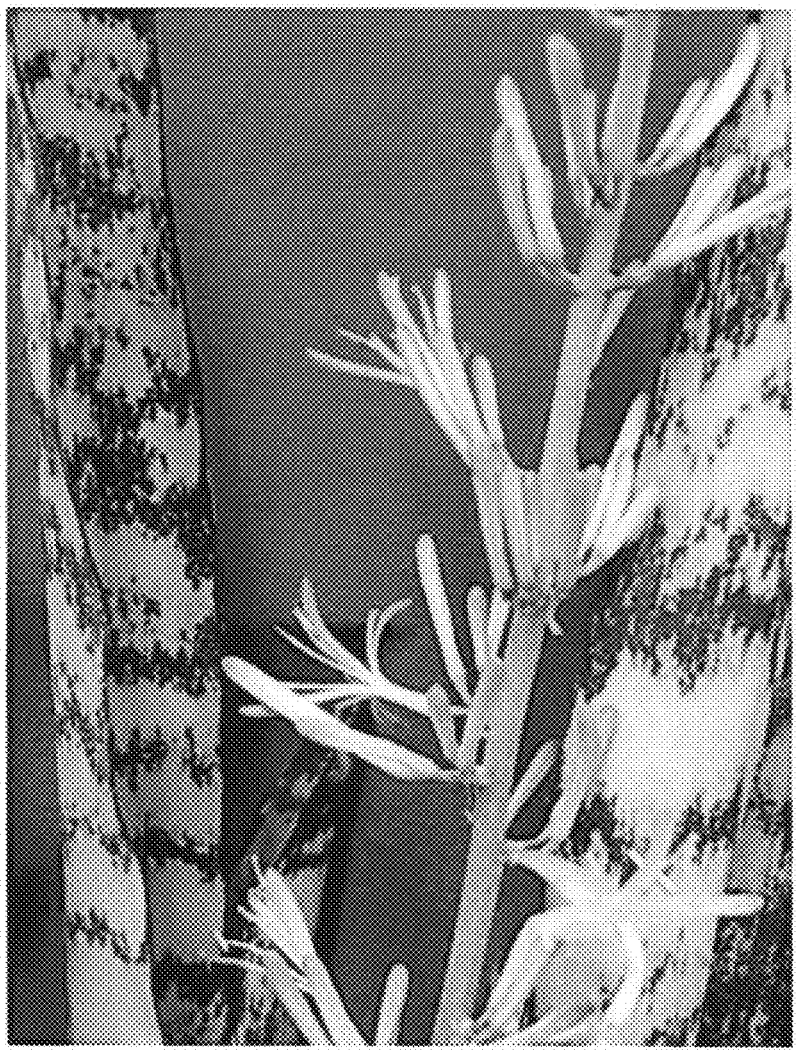
FIG. 4 shows a close up view of the inflorescence of 'Wintergreen'.

The new *Sansevieria* 'Wintergreen' has not been observed under all possible environmental conditions. The phenotype of the new cultivar may show phenotypical changes with variations in environment such as temperature, light intensity, and day length without any change in the genotype of the plant.

The aforementioned photographs, together with the following observations, measurements and values describe the new *Sansevieria* cultivar 'Wintergreen' as grown in open-field conditions at Bajo Los Rodriguez, San Ramón, Alajuela province, Costa Rica, which closely approximate those generally used in commercial practice. Average temperature at Bajo Los Rodriguez. is 26° C. during the day and 18° C. at night. Plants grow under natural light conditions.

This crop does not require constant fertilization, however, to increase production per area about 200 kg $ha^{-1}$ N, 150 kg $ha^{-1}$ of P and 100 kg $ha^{-1}$ K are required, the production is closely related with soil conditions in which they are grown.

Color references were made according to The Royal Horticultural Society Colour Chart (R.H.S., April 2009). The photographs and descriptions were made during the rainy season in Bajo Los Rodriguez, San Ramón, Alajuela province, Costa Rica when outdoor day average temperature was 26° C. The age of the plants described is 8 months.

Classification:

*Botanical.*—*Sansevieria trifasciata.*

*Variety denomination.*—Wintergreen.

Parentage: *Sansevieria trifasciata*, 'Bantels Sensation' (unpatented).

Optimal growth conditions:

*Light intensities.*—High adaptability to outdoor or indoor conditions.

*Temperature.*—Day: 26° C. to 32° C. Night: 18° C. to 23° C.

*Temperature tolerance.*—Tolerant to temperatures between 12° C. and 35° C.

*Fertilization.*—200, 150 and 100 kg $ha^{-1}$ of N, P and K.

*Growth regulators.*—Not necessary.

Propagation:

*Type.*—Vegetative, by rooted cuttings.

*Rooting habit description.*—Rizomes, with short roots.

*Time to initiate roots.*—15 to 22 days at 20-25° C.

*Faster time to produce a rooted cutting.*—About 60 to 90 days at 20-25° C.

Plant:

*General appearance and form.*—Height: About 80 cm when grown on the ground; About 45 cm when grown in a 21 cm size container. Spread: About 15 cm when grown on the ground; About 10 cm when grown in 21 cm size container. Form: Monocot; leaf bases arranged in a rosette around growing point. Shape: cylindrical.

*Growth rate and habit.*—About 2.5 cm per week; upright.

*Fragrance.*—None.

*Stem.*—Modified (Rhizome and foliage). Length: About 12 cm when grown in ground; About 8 cm when grown in 21 cm size container. Diameter: About 1.8-2.0 cm. Shape: round. Texture: rough. Color: RHS 17A. Strength: strong and durable. Internode length: About 0.5 mm to 0.7 mm.

Foliage:

*Quantity.*—About 5-7 leaves.

*Arrangement and attachment.*—Single, alternate; leaf bases arranged in a rosette around growing point.

*Leaf length.*—About 80 cm.

*Leaf width.*—About 3-5 cm.

*Overall shape of leaf.*—Lanceolated.

*Apex shape.*—Acute, triangular.

*Base shape.*—Plane.

*Margin.*—Sharp, smooth.

*Texture.*—Upper Surface: smooth and waxy texture. Under Surface: smooth and waxy texture.

*Pubescence.*—None.

*Color of mature leaf.*—Upper Surface: RHS135B and RHS138D. Lower Surface: RHS135B and RHS138D.

*Color of immature leaf.*—Upper Surface: RHS135B and RHS138D. Lower Surface: RHS135B and RHS138D.

*Venation.*—Pattern: longitudinal/parallel leaf shape. Color: None. Leaf fragrance: None.

Inflorescence description:

*Arrangement and type.*—Inflorescence.

*Orientation at opening.*—Out of the spike.

*Quantity.*—Per Plant with at least one open flower: One inflorescence per plant. About 28 flowers opened 2 weeks after appearance of the spike.

*Inflorescence size.*—Length: About 45 cm. Diameter: About 4 cm.

*Flower size.*—Length: About 4 cm. Diameter: About 15 mm. Depth: About 1 cm.

*Fragrance.*—None.

*Bud.*—Rate of opening: About one week, according to weather. Shape: long. Length: About 2 cm. Diameter: About 3 mm. Color: Apex: Light greenish yellow RHS 1C. Base: Yellowish white RHS 155D. Texture (both surfaces): smooth.

Petals:

*Quantity.*—6.

*Arrangement.*—Radial.

Reproductive organs:

*Androecium.*—Stamen: Number: 6 per flower. Length: About 1.5 cm. Color: Yellowish White, RHS 155D. Anther: Length: About 2 mm. Width: About 0.5 mm. Color: RHS 8D. Filament: Length: About 1.5 cm. Color: Yellowish White, RHS 155B. Pollen: Amount: moderate. Color: Yellowish white RHS 155D.

*Gynoecium.*—Pistil: Number: One per flower. Length: About 2.0 cm. Stigma: Length: About 0.6 mm. Width: About 1.0 mm. Color: Yellowish white RHS 155D. Style: Length: About 2.2 cm. Color: Yellowish White, RHS 155B. Ovary: Length: About 4 mm. Width: About 2.0 mm. Color: RHS 150D.

Weather resistance: Drought tolerant.

Disease/pest resistance: High resistance to antrachnose (*Colletotrichum sansevierae*).

Disease/pest susceptibility: Not observed so far.

I claim:

1. A new and distinct *Sansevieria* plant named 'Wintergreen', substantially as illustrated and described herein.

* * * * *